US010899356B2

(12) United States Patent
Mochizuki et al.

(10) Patent No.: US 10,899,356 B2
(45) Date of Patent: Jan. 26, 2021

(54) DROWSINESS PREVENTION DEVICE, DROWSINESS PREVENTION METHOD, AND RECORDING MEDIUM

(71) Applicant: Panasonic Intellectual Property Management Co., Ltd., Osaka (JP)

(72) Inventors: Makoto Mochizuki, Kanagawa (JP); Shinichi Shikii, Nara (JP); Masanobu Kanaya, Kanagawa (JP); Wataru Nakai, Tokyo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 16/558,268

(22) Filed: Sep. 2, 2019

(65) Prior Publication Data

US 2019/0382026 A1 Dec. 19, 2019

Related U.S. Application Data

(63) Continuation of application No. PCT/JP2017/045903, filed on Dec. 21, 2017.

(30) Foreign Application Priority Data

Mar. 30, 2017 (JP) ................. 2017-068132

(51) Int. Cl.
*B60W 40/08* (2012.01)
*B60H 3/00* (2006.01)
(Continued)

(52) U.S. Cl.
CPC ........... *B60W 40/08* (2013.01); *B60H 3/0035* (2013.01); *B60W 50/14* (2013.01); *B60W 50/16* (2013.01);
(Continued)

(58) Field of Classification Search
CPC combination set(s) only.
See application file for complete search history.

(56) References Cited

U.S. PATENT DOCUMENTS

| 2010/0214087 A1 | 8/2010 | Nakagoshi et al. | |
| 2015/0328985 A1* | 11/2015 | Kim | A61B 5/163 |
| | | | 108/272 |

FOREIGN PATENT DOCUMENTS

| JP | 2008-181327 | 8/2008 |
| JP | 2010-009413 | 1/2010 |
| JP | 5228970 B | 7/2013 |

OTHER PUBLICATIONS

International Search Report of PCT application No. PCT/JP2017/045903 dated Mar. 13, 2018.
(Continued)

*Primary Examiner* — Travis R Hunnings
(74) *Attorney, Agent, or Firm* — Greenblum & Bernstein, P.L.C.

(57) ABSTRACT

A drowsiness prevention device includes a psychological state estimator and a controller. The psychological state estimator estimates a psychological state of an occupant, based on a state of the occupant detected by a detection device. The controller causes an output device to output a first warning and a second warning which are for alerting the occupant. The psychological state estimator estimates a first psychological state of the occupant which is before the first warning is output and a second psychological state of the occupant which is after the first warning is output. The controller determines details of a second warning, based on only the second psychological state or based on both the first psychological state and the second psychological state.

10 Claims, 8 Drawing Sheets

(51) Int. Cl.
*B60W 50/14* (2020.01)
*B60W 50/16* (2020.01)
*G06K 9/00* (2006.01)

(52) U.S. Cl.
CPC ... *G06K 9/00845* (2013.01); *B60W 2050/143* (2013.01); *B60W 2420/42* (2013.01); *B60W 2540/22* (2013.01)

(56) References Cited

OTHER PUBLICATIONS

James A. Russell, "A Circumplex Model of Affect", Journal of Personality and Social Psychology, 1980, vol. 39, No. 6, pp. 1161-1178.
Notice of Reasons for Refusal in Japan dated May 26, 2020 for the related Japanese Patent Application No. 2017-068132, together with an English language translation thereof.

* cited by examiner

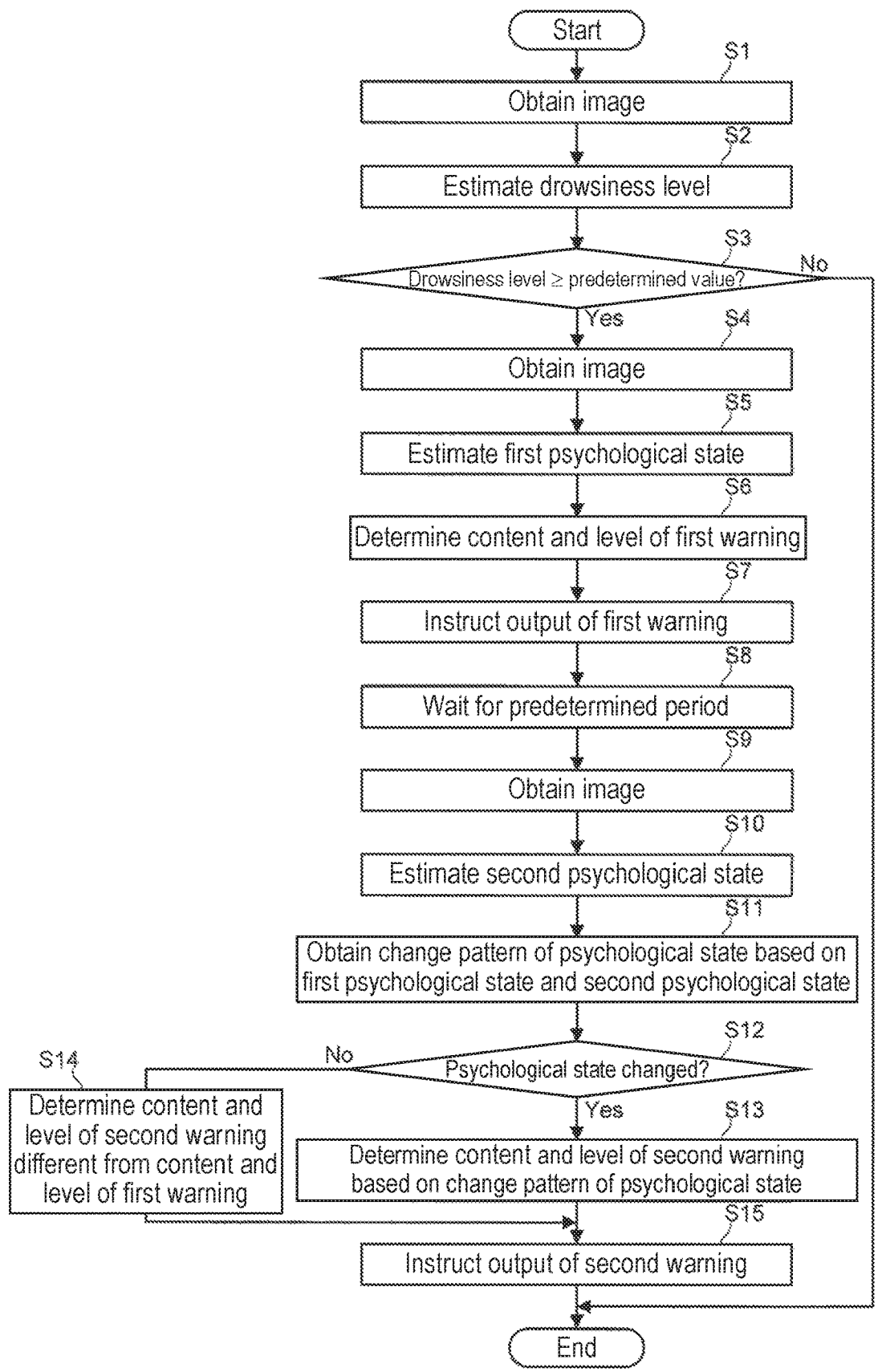

DROWSINESS PREVENTION DEVICE, DROWSINESS PREVENTION METHOD, AND RECORDING MEDIUM

CROSS-REFERENCE TO RELATED APPLICATIONS

This application is a continuation of the PCT International Application No. PCT/JP2017/045903 filed on Dec. 21, 2017, which claims the benefit of foreign priority of Japanese patent application No. 2017-068132 filed on Mar. 30, 2017, the contents all of which are incorporated herein by reference.

BACKGROUND

1. Technical Field

The present disclosure relates to a drowsiness prevention device, a drowsiness prevention method, and a recording medium on which a program is stored.

2. Description of the Related Art

In recent years, a driver monitoring technique has been developed in which drowsiness of a driver is detected by using a camera mounted inside the vehicle for capturing an image of the face of the driver and a warning or alert display is provided to prevent accidents caused by drowsy driving.

For example, a technique has been proposed in which the distance between the upper and lower eyelids of the driver (inter-eyelid distance) is calculated by using an in-vehicle camera, and the level of drowsiness of the driver is estimated based on the inter-eyelid distance (six levels ranging from "does not look sleepy at all" to "asleep"). A warning or alert display is then provided when the level of drowsiness exceeds a predetermined value.

Japanese Patent No. 5228970 discloses a method that assumes the drowsiness is not removed by a single warning. After the drowsiness is detected and a warning is given to the driver, in order to confirm the effect of the warning, the level of drowsiness is estimated again after a predetermined period. When the drowsiness is detected again, a warning or alert is continuously given to the driver as an additional warning.

SUMMARY

The present disclosure provides a drowsiness prevention device, a drowsiness prevention method, and a recording medium on which a program is stored, which have been improved to be capable of waking a drowsy occupant earlier.

A drowsiness prevention device according to one aspect of the present disclosure includes a psychological state estimator and a controller. The psychological state estimator estimates a psychological state of an occupant based on a state of the occupant detected by a detection device. The controller causes an output device to output a first warning and a second warning which are for alerting the occupant. The psychological state estimator estimates a first psychological state of the occupant which is before the first warning is output and a second psychological state of the occupant which is after the first warning is output. The controller determines details of a second warning based on only the second psychological state or based on both the first psychological state and the second psychological state.

A drowsiness prevention method according to another aspect of the present disclosure is performed by the drowsiness prevention device. The drowsiness prevention method includes: estimating a first psychological state; causing a first warning to be output after estimating the first psychological state; estimating the second psychological state; determining details of a second warning; and causing the second warning to be output after determining the details of the second warning. When estimating the first psychological state, the first psychological state of the occupant is estimated based on the state of the occupant detected by a detection device. When causing the first warning to be output, the output device is caused to output the first warning which is for alerting the occupant. When estimating the second psychological state, the second psychological state of the occupant which is after the first warning is output is estimated based on the state of the occupant detected by the detection device. When determining the details of the second warning, details of the second warning for alerting the occupant is determined based on only the second psychological state or based on both the first psychological state and the second psychological state. When causing the second warning to be output, the output device is caused to output the second warning.

A non-transitory recording medium according to still another aspect of the present disclosure, stores a program executed by a computer included in the drowsiness prevention device. The program causes the computer to execute: estimating a first psychological state; causing a first warning to be output; estimating a second psychological state; determining details of a second warning; and causing the second warning to be output after determining the details of the second warning. When estimating the first psychological state, the first psychological state of the occupant is estimated based on a state of the occupant detected by a detection device. When causing the first warning to be output, the output device is caused to output the first warning which is for alerting the occupant. When estimating a second psychological state, the second psychological state of the occupant which is after the first warning is output is estimated based on a state of the occupant detected by the detection device. When determining the details of the second warning, details of the second warning for alerting the occupant is determined based on only the second psychological state or based on both the first psychological state and the second psychological state. When causing the second warning to be output, the output device is caused to output the second warning.

It is to be noted that an aspect of the present disclosure changed among a method, a device, a system, a recording medium (including a non-transitory computer readable recording medium), a computer program, and so forth is also effective as an aspect of the present disclosure.

According to the present disclosure, it is possible to wake a drowsy occupant earlier.

BRIEF DESCRIPTION OF DRAWINGS

FIG. 3 is a flowchart of an example of an operational flow of a drowsiness prevention device according to a first exemplary embodiment.

DETAILED DESCRIPTION OF PREFERRED EMBODIMENTS

Prior to describing the exemplary embodiments of the present disclosure, problems in the conventional technique will be briefly described.

In order to determine the effectiveness of an initial warning in accordance with Japanese Patent No. 5228970, it is necessary to estimate the level of drowsiness again after the initial warning. However, in general estimation of the level of drowsiness, typically in PERCLOS (percentage eye closure ratio, the percentage of eye closure over a given period), it is necessary to detect the frequency of eyelid opening and closing over a period ranging from one to three minutes, approximately. In other words, it takes about one to three minutes to determine the effectiveness of the initial warning. Hence, the delay between the time when the driver feels drowsy after the initial warning and the time when the initial warning is determined to be ineffective results in delaying waking of the driver by an additional warning.

Hereinafter, the exemplary embodiments of the present disclosure will be described in detail with reference to the drawings.

First Exemplary Embodiment

Figure 1:
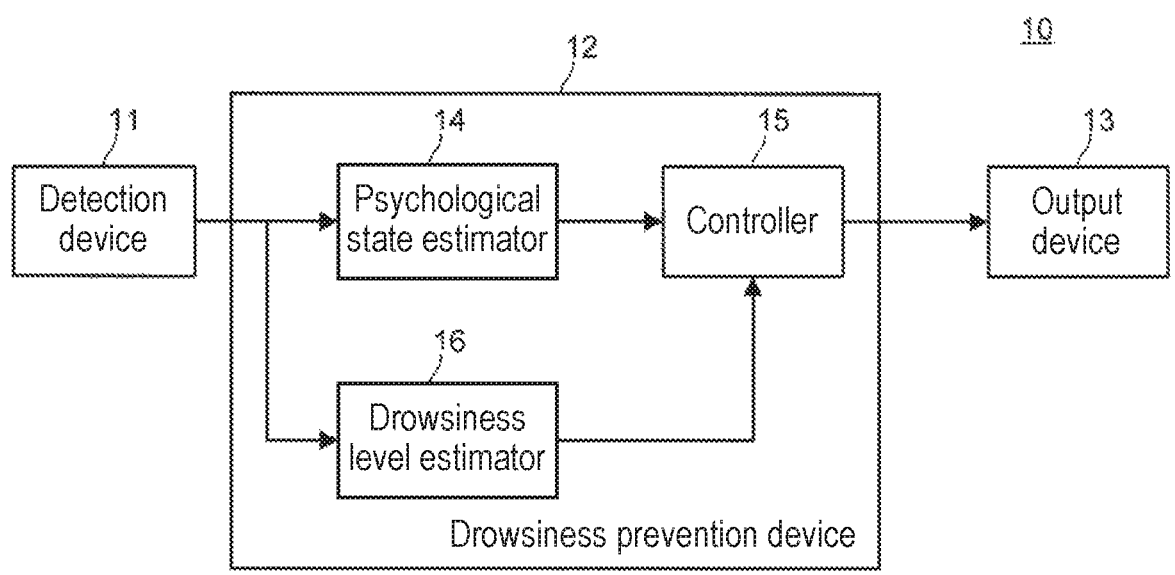
FIG. 1 illustrates drowsiness prevention system including a drowsiness prevention device according to exemplary embodiments of the present disclosure.

FIG. 1 illustrates drowsiness prevention system 10 according to exemplary embodiments of the present disclosure. Drowsiness prevention system 10 includes detection device 11, drowsiness prevention device 12, and output device 13. Drowsiness prevention device 12 includes psychological state estimator 14 and controller 15. In one example, drowsiness prevention device 12 further includes drowsiness level estimator 16.

Detection device 11 detects the state of a portion of the body of an occupant (for example, driver). In one example, the state of the occupant is a state of a portion of the body of the occupant. Examples of the portion of the body of the occupant include a face and a wrist. In another example, the state of an occupant is biological information of the occupant.

In one example, detection device 11 includes a passive detector which detects reflection of light from an external light source such as sunlight, electromagnetic waves, sound waves or the like, and captures an image of the face of the occupant. Examples of the passive detector include a charge-coupled device (CCD) image sensor and a metal oxide semiconductor (MOS) image sensor which are capable of receiving visible light. In another example, detection device 11 includes an optical detector which measures the heart rate, pulse rate, and the like of the occupant, to measure biological information such as the heart rate or the pulse rate appearing in the wrist of the occupant.

Drowsiness prevention device 12 instructs output device 13 to output a warning, based on the image or biological information of the occupant obtained from detection device 11. Drowsiness prevention device 12 includes, for example, a central processing unit (CPU), a read only memory (ROM), and a random access memory (RAM). The CPU, for example, reads out, from the ROM, the program corresponding to the processing details, develops the program in the RAM, and performs central control on the operations of the respective blocks of drowsiness prevention device 12 in coordination with the developed program.

Output device 13 outputs a warning to the occupant in response to the instruction sent from drowsiness prevention device 12. Here, the warning includes an initial warning (first warning) and an additional warning (second warning). In one example, output device 13 includes at least one of a display (visual indicator), a means which outputs sound (audio indicator), a means which generates an odor (olfactory indicator), and a means which affects sense of touch (tactile indicator).

In one example, the visual indicator is an instrument panel which displays information related to the state of a vehicle, such as vehicle speed or engine rotational speed. In another example, the visual indicator is a display of a car navigation system which displays map of the area around the current position, and information related to the position of the vehicle, such as route to the destination. The visual indicator outputs a warning by, for example, blinking the screen, increasing the brightness of the screen, changing the color of the screen, or displaying messages such as "please drive safely" or "please drive safely and calmly". In one example, the blinking cycle of the screen blinked by the visual indicator, the level of brightness of the screen increased by the visual indicator, and the color of the screen changed by the visual indicator are adjustable by a user.

In one example, the audio indicator is an in-vehicle loudspeaker which changes an audio signal from an in-vehicle audio into sound. The audio indicator outputs a warning by generating a beeping sound such as "bip" or "beep", audio messages such as "please drive safely" or "please drive safely and calmly", or music appropriate for waking the occupant. In one example, the level of sound generated by the audio indicator is adjustable by a user.

In one example, the olfactory indicator is an odor generating device which generates woodsy smells such as *eucalyptus*, or herbal smells such as peppermint which have an effect of improving the concentration of the occupant. For example, the odor generating device includes a fragrance which generates an odor, and generates odor by sending air to the fragrance. In one example, the intensity of odor generated by the odor display means is adjustable by a user.

In one example, the tactile indicator is a vibrator which vibrates a portion of the skin of the occupant. The vibrator is an oscillator attached to a portion, such as a steering wheel or seat belt, which constantly contacts the occupant or which has a lot of opportunities to touch the occupant. In one example, the magnitude of vibration generated by the vibrator is adjustable by a user.

In one example, the tactile indicator is an in-vehicle air conditioner which is capable of sending cool air. In one example, the temperature and the strength of the cool air are adjustable by a user.

Psychological state estimator 14 estimates a first psychological state and a second psychological state of the occupant based on the image or the biological information obtained from detection device 11. Here, the first psychological state refers to a psychological state of the occupant before output device 13 outputs the first warning. The second psychological state refers to a psychological state of the occupant after output device 13 outputs the first warning and before output device 13 outputs the second warning. In one example, each of the first psychological state and the second psychological state is emotion.

Figure 2:
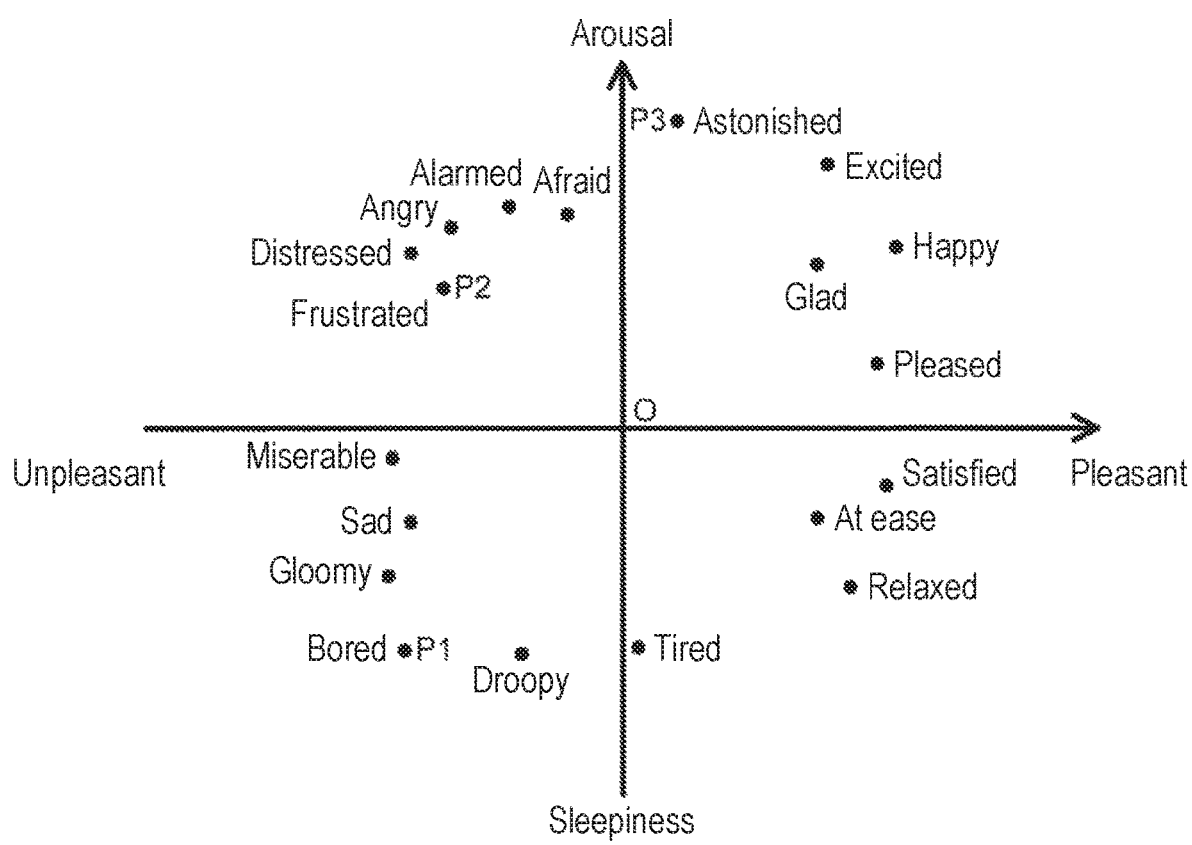
FIG. 2 illustrates an example of emotion according to the exemplary embodiments of the present disclosure.

FIG. 2 illustrates an example of emotions (or affects) according to the exemplary embodiments of the present disclosure. The emotions illustrated in FIG. 2 are classified in accordance with the circumplex model of affect of Russell (see James A. Russell, "A Circumplex Model of Affect" Journal of Personality and Social Psychology 1980, Vol. 39, No. 6, pp. 1161-1178). In FIG. 2, the horizontal axis and the vertical axis crossing at the origin O respectively represent a pleasantness axis and an arousal axis. Points (hereinafter, referred to as emotional points) corresponding to human emotions (such as "bored", "relaxed", "frustrated", and "astonished"), respectively, are plotted.

In FIG. 2, a given emotional point is represented as a two dimensional vector having, as components, a coordinate value ranging from −1.0 to +1.0, inclusive, along the pleasantness axis and a coordinate value ranging from −1.0 to +1.0, inclusive, along the arousal axis. In the following description, the two dimensional vector is referred to as an emotional vector.

The emotional vector indicates the type and the degree of an emotion. In FIG. 2, when an emotional point exists in the direction of the emotional vector, the emotion corresponding to the emotional point is the type of the emotion indicated by the emotional vector. In contrast, when no emotional point exists in the direction of the emotional vector, the emotion corresponding to the emotional point which exists in the direction closest to the emotional vector is the type of emotion indicated by the emotional vector, for example. The magnitude of the emotional vector indicates the degree of the emotion.

Another example of emotions is emotions classified into seven types including six basic emotions, happiness, joy, disgust, anger, fear, and surprise, which appear in the facial expression, and neutral.

Psychological state estimator 14 estimates the psychological state of the occupant. Known techniques can be used for estimating the psychological state.

In one example, estimation models for estimating the emotional vector in the circumplex model of affect of Russell are generated in advance by machine learning, etc., based on the positional relationship of the feature points of the face, and the generated estimation models are stored in a non-volatile storage device (not illustrated) of psychological state estimator 14. Subsequently, during the operation of drowsiness prevention device 12, psychological state estimator 14 estimates the emotional vector by using the estimation models, based on the positions of the feature points detected from the image of the occupant.

Subsequently, the emotion is estimated by using the circumplex model of affect of Russell, based on the estimated emotional vector.

In another example, estimation models for estimating the above described seven types of emotions based on the positional relationship of the feature points of the face, such as the outer corner of the eye, the inner corner of the eye, and the corners of the mouth, are generated in advance by machine learning, etc. The generated estimation models are then stored in a non-volatile storage device (not illustrated) of psychological state estimator 14. Subsequently, during the operation of drowsiness prevention device 12, psychological state estimator 14 estimates the emotion by using the estimation models, based on the positions of the feature points detected from the image of the occupant.

In another example, in addition to the image of the occupant, or instead of the image of the occupant, estimation models for estimating emotion based on the feature amount, such as heart rate or the pulse rate of the occupant, are used.

Now, reference is made to FIG. 1 again. Controller 15 causes output device 13 to output the first warning and the second warning which are for alerting the occupant. In one example, controller 15 determines details of the first warning based on the first psychological state. In another example, controller 15 determines details of the second warning based on the second psychological state. In yet another example, controller 15 determines the details of the second warning based on the first and second psychological states. Details of the determination of the details of the first warning and the second warning will be described later with reference to Table 1 to Table 5.

Drowsiness level estimator 16 estimates a level of drowsiness of the occupant. In one example, drowsiness level estimator 16 estimates the level of drowsiness based on the image of the occupant obtained from detection device 11.

For example, drowsiness level estimator 16 determines whether or not the occupant is closing his or her eyes based on the image of the occupant, and estimates the level of drowsiness by calculating the PERCLOS value as the level of drowsiness to estimate the level of drowsiness. Moreover, for example, drowsiness level estimator 16 estimates the level of drowsiness by calculating the degree of eye opening when the occupant is opening his or her eyes, based on the image of the occupant.

In one example, controller 15 causes output device 13 to output the first warning based on the comparison between the level of drowsiness and a predetermined value. Here, the predetermined value is a threshold limit value of the level of drowsiness to be determined that the occupant is asleep. For example, when the predetermined value of the PERCLOS value is a given value in a range from 50% to 100%, inclusive, and the estimated PERCLOS value is equal to or greater than the predetermined value, controller 15 causes output device 13 to output the first warning. Moreover, for example, when a predetermined value of the degree of eye opening is a given value in a range from 0% to 50%, inclusive and the estimated degree of eye opening is less than or equal to the predetermined vale, controller 15 causes output device 13 to output the first warning.

FIG. 3 is a flowchart of an example of an operational flow of drowsiness prevention device 12 according to the first exemplary embodiment. For example, this processing is implemented by the CPU of drowsiness prevention device 12 reading out the program stored in the ROM and periodically executing the program, along with the activation of the engine of the vehicle. The operational flow illustrated in FIG. 3 is periodically and repeatedly performed. For the sake of simplicity, an example will be described where a psychological state of the occupant is an emotion and a passive detector which captures an image is used as detection device 11. The following description, however, is also applicable to other cases.

First, in step S1, drowsiness prevention device 12 obtains an image of the occupant from detection device 11 (processing performed as drowsiness level estimator 16).

In step S2, drowsiness prevention device 12, estimates the level of drowsiness of the occupant, based on the image obtained in step S1 (processing performed as drowsiness level estimator 16). In one example, drowsiness level estimator 16 extracts the image of the eyes of the occupant from the obtained image, and estimates the level of drowsiness from the extracted image of the eyes, based on the percentage of eye-closing time over a predetermined period.

In step S3, drowsiness prevention device 12 determines whether or not the level of drowsiness is equal to or greater than a predetermined value (processing performed as controller 15). When the level of drowsiness is less than the predetermined value (No in step S3), the occupant is determined not to be asleep. The flow ends here. In contrast, when the level of drowsiness is equal to or greater than the predetermined value (Yes in step S3), the occupant is determined to possibly be asleep. The flow proceeds to step S4.

In step S4, drowsiness prevention device 12 obtains an image of the occupant from detection device 11 (processing performed by psychological state estimator 14). The image of the occupant obtained by drowsiness level estimator 16 in step S1 may be used as the image of the occupant in step S4.

In step S5, drowsiness prevention device 12 estimates the first psychological state based on the image obtained in step S4 (processing performed as psychological state estimator 14). Here, the first psychological state refers to the psychological state of the occupant before output device 13 outputs the first warning in step S7 to be described later.

In one example, the first psychological state is one of emotions classified in accordance with the circumplex model of emotion of Russel. Here, FIG. 4A and FIG. 4B are referred.

Figure 4A:
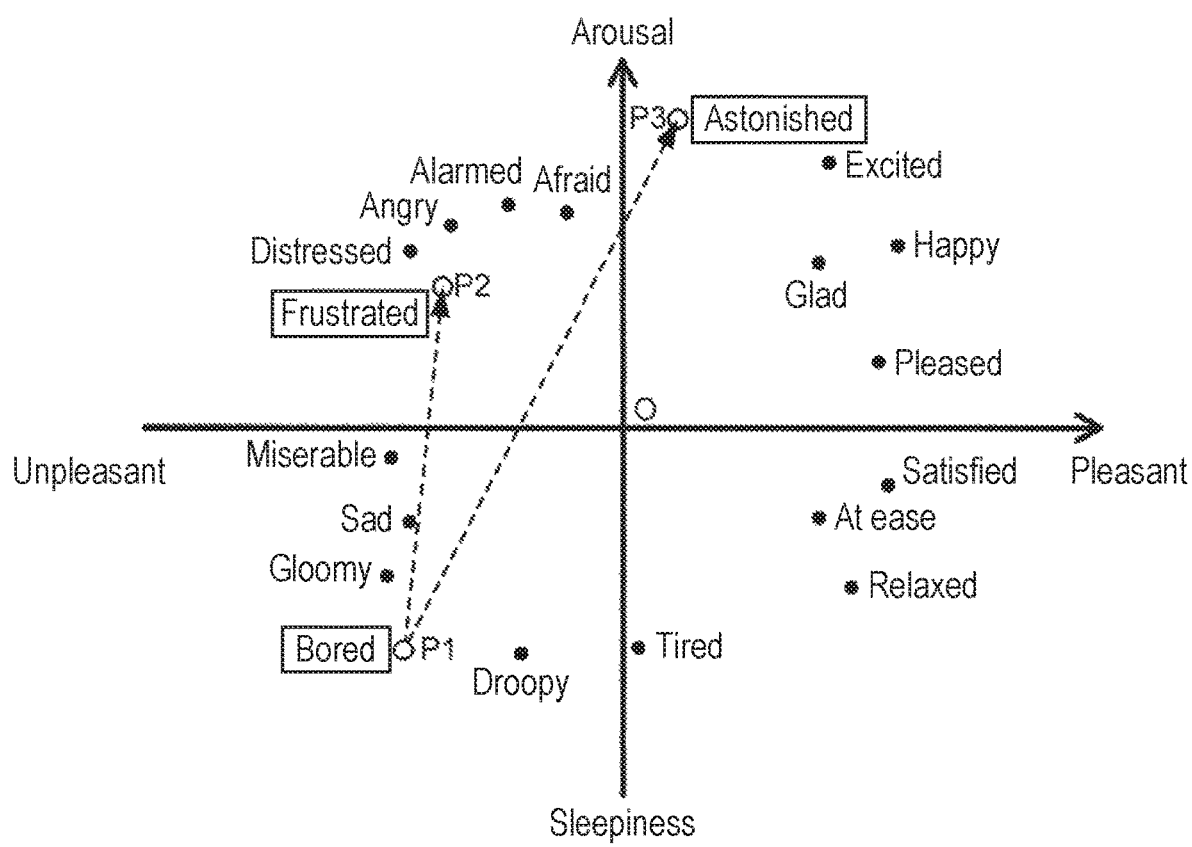
FIG. 4A illustrates emotional changes according to the first exemplary embodiment.
Figure 4B:
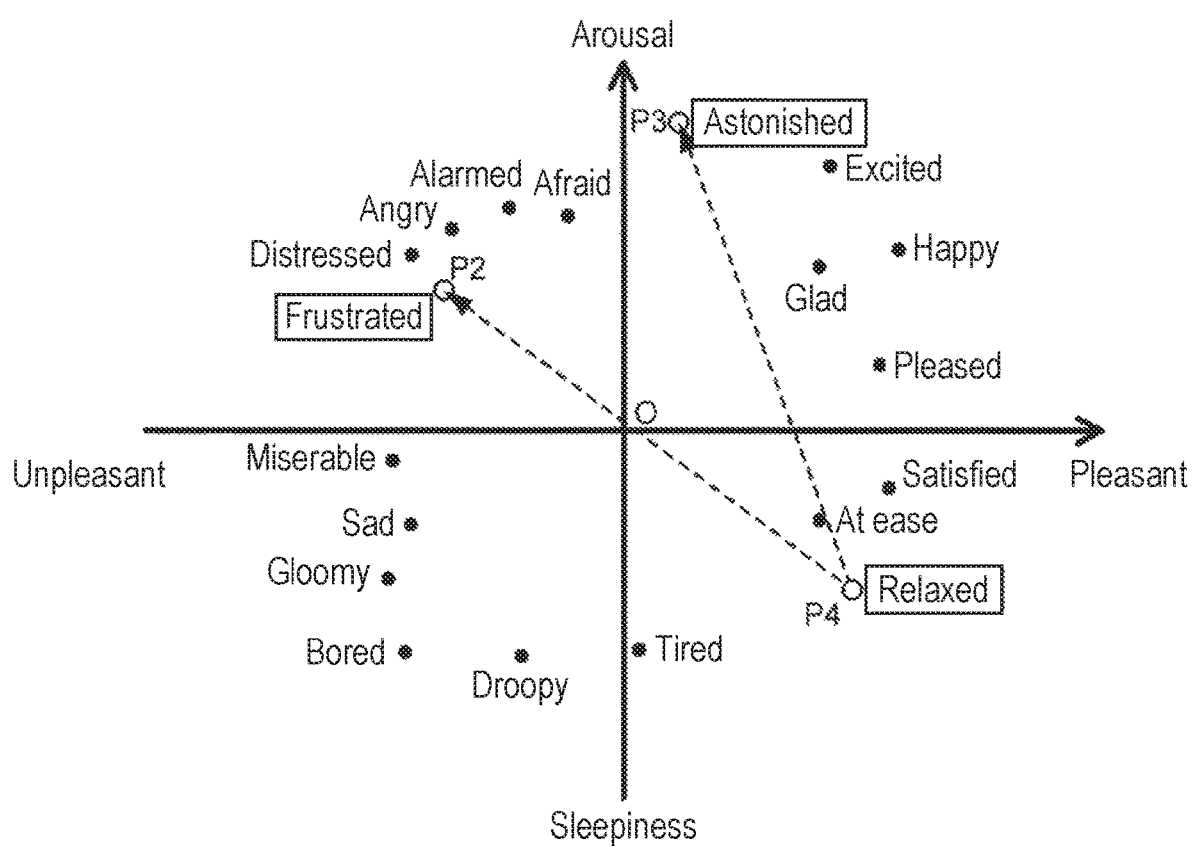
FIG. 4B illustrates emotional changes according to the first exemplary embodiment.

Each of FIG. 4A and FIG. 4B illustrates emotional changes according to the first exemplary embodiment. For example, when the first psychological state is "bored", as illustrated in FIG. 4A, the first psychological state is represented by emotional point P1 corresponding to "bored". Moreover, for example, when the first psychological state is "relaxed", as illustrated in FIG. 4B, the first psychological state is represented by emotional point P4 corresponding to "relaxed".

Now, FIG. 3 is referred again. In step S6, drowsiness prevention device 12 determines the content of indication and the level of the first warning (processing performed as controller 15).

In one example, controller 15 determines the content of indication and the level of the first warning based on the first psychological state. For example, when the first psychological state is "bored", the indication content for the first warning is a combination of the sound "bip" and the vibration of the steering. Moreover, for example, when the first psychological state is "relaxed", the indication content for the first warning is the sound "bip" only. Moreover, in one example, the level of the first warning is determined in accordance with the magnitude of the emotional vector which indicates the first psychological state.

In another example, controller 15 determines the content of indication and the level of the first warning to predetermined kind and level.

In step S7, drowsiness prevention device 12 instructs output device 13 to output the first warning (processing performed by controller 15). In response to the instruction, output device 13 outputs the first warning.

In step S8, drowsiness prevention device 12 stands by for a predetermined period (processing performed as controller 15). It is considered that a certain period of time is required from the time when output device 13 outputs the first warning till the time when the occupant reacts to the first warning. Accordingly, controller 15 stands by for the predetermined period in order to prevent subsequent steps S9 to S15 from being performed before the occupant reacts to the first warning. In one example, the predetermined period is a given period less than or equal to ten seconds, and for example, three seconds. Moreover, in one example, the predetermined period is predetermined in accordance with the content and the level of the first warning.

In step S9, drowsiness prevention device 12 obtains an image of the occupant from detection device 11 (processing performed as psychological state estimator 14). In one example, the image obtained in step S9 is an image of the occupant captured after the first warning is output.

In the above example, processing in step S9 is performed after standing by the predetermined period in step S8, but the present disclosure is not limited to the example. For example, in step S8, drowsiness prevention device 12 may stand by till the occupant changes the expression. Moreover, for example, when step S8 is skipped and the driver changes the expression in step S9, it may be that the image of the occupant is obtained from detection device 11.

In step S10, drowsiness prevention device 12 estimates the second psychological state which is after the first warning is output, based on the image obtained in step S9 (processing performed as psychological state estimator 14). Here, the second psychological state refers to the psychological state of the occupant after output device 13 has output the first warning in step S7. The processing details in step S10 are similar to the processing details in step S5 in which the first psychological state is estimated.

In step S11, drowsiness prevention device 12 obtains the change pattern of the psychological state based on the first psychological state and the second psychological state (processing performed as controller 15). Here, FIG. 4A and FIG. 4B are referred again.

The arrow directing from emotional point P1 to emotional point P2 illustrated in FIG. 4A indicates an emotional change from "bored" corresponding to emotional point P1 to "frustrated" corresponding to emotional point P2. In this case, the first psychological state is "bored", and the second psychological state is "frustrated". The change pattern of the psychological state is from "bored" to "frustrated". In a similar manner, the arrow directing from emotional point P1 to emotional point P3 illustrated in FIG. 4A indicates an emotional change from "bored" corresponding to emotional point P1 to "astonished" corresponding to emotional point P3.

In a similar manner, the arrow directing from emotional point P4 to emotional point P2 illustrated in FIG. 4B indicates an emotional change from "relaxed" corresponding to emotional point P4 to "frustrated" corresponding to emotional point P2. In this case, the first psychological state is "relaxed", and the second psychological state is "frustrated". The change pattern of the psychological state is from "relaxed" to "frustrated". In a similar manner, the arrow directing from emotional point P4 to emotional point P3 illustrated in FIG. 4B indicates an emotional change from "relaxed" corresponding to emotional point P4 to "astonished" corresponding to emotional point P3.

In step S12, drowsiness prevention device 12 determines whether or not a change in psychological state is seen in the change pattern of the psychological state (processing performed as controller 15). When it is determined that the psychological state change is seen (Yes in step S12), the flow proceeds to step S13. In contrast, when it is determined that no psychological state change is seen (No in step S12), it is considered that a warning other than the first warning is necessary. The flow proceeds to step S14.

In step S13, drowsiness prevention device 12 determines the content of indication and the level of the second warning, based on the change pattern of the psychological state (processing performed as controller 15).

In one example, the second warning depends on the second psychological state. For example, when the second psychological state is "frustrated", the indication content for the second warning is a combination of the audio of "please drive safely" and generation of cool air. Moreover, for example, when the second psychological state is "astonished", the indication content for the second warning is only the audio of "please drive safely and calmly".

The above example can be summarized as in Table 1 and Table 2 as below.

TABLE 1

Example of Relationship between First and Second Psychological States and Content of First and Second Warning

|  |  | Second psychological state | |
| --- | --- | --- | --- |
|  |  | Frustrated | Astonished |
| First psychological state | Bored | Warning pattern 1 → Warning pattern 3 | Warning pattern 1 → Warning pattern 4 |
|  | Relaxed | Warning pattern 2 → Warning pattern 3 | Warning pattern 2 → Warning pattern 4 |

TABLE 2

Description of Warning Pattern in Table 1

| Warning pattern | Details of warning |
| --- | --- |
| 1 | Sound "bip" + vibration of steering |
| 2 | Sound "bip" |
| 3 | Audio "please drive safely" + cool air (*control for calming frustrated feelings) |
| 4 | Audio "please drive safely and calmly" (*message for calming astonished feelings) |

In Table 1, and Table 3 and Table 5 to be described later, the warning patterns before and after the arrows are respectively the first warning and the second warning. As illustrated in Table 1, in the above example, the second warning does not depend on the first psychological state (in other words, the second warning depends only on the second psychological state).

In another example, as illustrated in the following Table 3 and Table 4, the second warning depends on both the first psychological state and the second psychological state.

TABLE 3

Another Example of Relationship between First and Second Psychological States and Content of First and Second Warning

|  |  | Second psychological state | |
| --- | --- | --- | --- |
|  |  | Frustrated | Astonished |
| First psychological state | Bored | Warning pattern 1 → Warning pattern 5 | Warning pattern 1 → Warning pattern 6 |
|  | Relaxed | Warning pattern 2 → Warning pattern 7 | Warning pattern 2 → Warning pattern 8 |

TABLE 4

Description of Warning Pattern in Table 3

| Warning pattern | Details of warning |
| --- | --- |
| 5 | Audio "please drive safely and calmly" (*the number of indication of warning is less, and the degree of warning is less than the first warning,) |
| 6 | Sound "bip" (*the number of indication of warning is less, or the degree of warning is less than the first warning) |
| 7 | Cool air (*warning by the content of warning different from the first warning) |
| 8 | Audio "please drive safely and calmly" (*warning is made by content of warning same as the first warning, and the degree of warning is less than the first warning) |

Moreover, in another example, the second warning depends on one component (for example, pleasantness axis component) of the emotional vector of the first psychological state and one component (for example, pleasantness axis component) of the emotional vector of the second psychological state. For example, the second warning is determined based on Table 5 as below.

TABLE 5

Another Example of Relationship between First and Second Psychological States and Content of First and Second Warning

|  |  | Second psychological state | |
| --- | --- | --- | --- |
|  |  | Unpleasant | Pleasant |
| First psychological state | Unpleasant | Warning pattern 1 → Warning pattern 5 | Warning pattern 1 → Warning pattern 6 |
|  | Pleasant | Warning pattern 2 → Warning pattern 7 | Warning pattern 2 → Warning pattern 8 |

In one example, the level of the second warning is determined in accordance with the magnitude of the emotional vector which indicates the second psychological state.

Moreover, when it is determined that the psychological state of the occupant has been changed, it is also considered that the object of waking the occupant has been achieved depending on the second psychological state (for example, when the second psychological state is changed to "astonished"). Accordingly, in one example, in step S13, controller 15 sets the level of the second warning to zero, in other words, determines not to cause output device 13 to output the second warning.

In contrast, in step S14, drowsiness prevention device 12 determines the indication content and the level of the second warning to be different from the first warning in at least one of the content and the level (processing performed as controller 15).

In one example, controller 15 determines the second warning means to be the same as the first warning means, and determines the level of the second warning to be greater than the level of the first warning. Accordingly, even when the first warning does not make any effect, the second warning which is expected to be more effective on the occupant can be output to the occupant.

In another example, controller 15 determines the content of the second warning to be different from the content of the first warning. For example, when the first warning is an indication which affects visual sense, the second warning is determined to be an indication which affects senses other than visual sense (for example, auditory, olfactory, and touch). Accordingly, it is possible to prevent the occupant from getting used to the warnings. Moreover, it is possible to output, to an occupant with visual or hearing impairment, the second warning which is expected to be more effective on such an occupant.

In step S15, drowsiness prevention device 12 instructs output device 13 to output the second warning (processing performed as controller 15). In response to the instruction, output device 13 outputs the second warning.

In one example, in step S13, when controller 15 determines not to cause output device 13 to output the second warning, output device 13 outputs no warning in step S15.

As described above, drowsiness prevention device 12 according to the first exemplary embodiment includes psychological state estimator 14 and controller 15. Psychological state estimator 14 estimates the psychological state of the occupant based on the state of the occupant detected by detection device 11. Controller 15 causes output device 13 to output the first warning and the second warning which are for alerting the occupant. Moreover, psychological state estimator 14 estimates the first psychological state of the occupant which is before the first warning is output and the second psychological state of the occupant which is after the first warning is output. Moreover, controller 15 determines the details of the second warning based on only the second psychological state or based on both the first psychological state and the second psychological state.

According to the first exemplary embodiment, it is not necessary to perform drowsiness estimation which requires time in order to determine the effectiveness of the initial warning. Accordingly, it is possible to wake an occupant earlier even the occupant requires an additional warning to be woken.

Moreover, according to the first exemplary embodiment, the reaction of the occupant to the initial warning is taken into consideration when an additional warning is given. Accordingly, compared with the case where the reaction is not taken into consideration, it is possible to output, to the occupant, an additional warning which is expected to be more effective to the occupant.

Moreover, according to the first exemplary embodiment, a warning which is unlikely to provide waking effects, such as a warning which has a low warning intensity or a warning of which modality (display means) is inappropriate (for example, an auditory warning is inappropriate to an occupant whose hearing is bad) is less likely to be provided continuously to the occupant as an additional warning. Accordingly, it is possible to reduce the possibility of occurrence of such problems that expected waking effects cannot be obtained or recovery after being woken takes time.

As described above, according to the first exemplary embodiment, it is possible to wake an occupant earlier by providing an additional warning with the intensity or strength and modality suitable for the occupant.

Second Exemplary Embodiment

Figure 5:
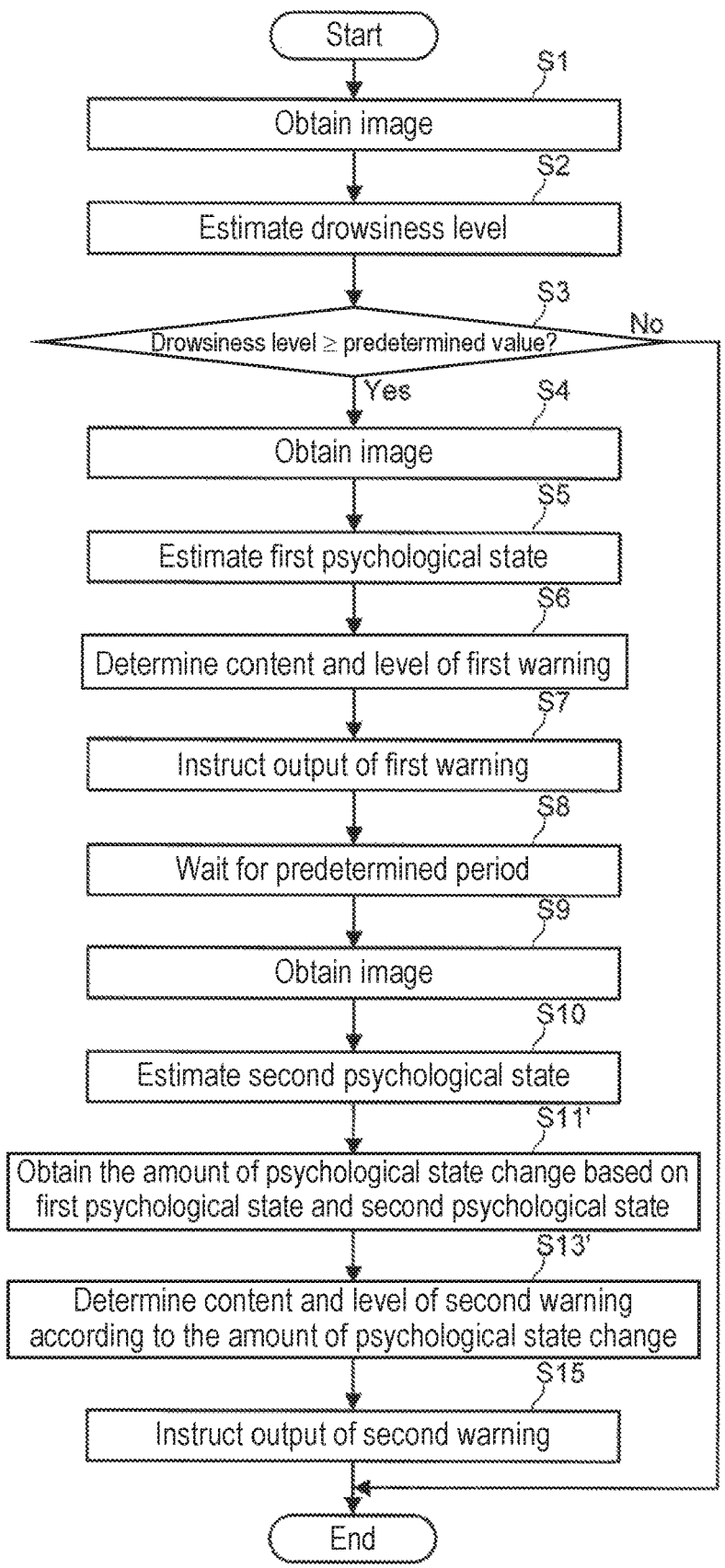
FIG. 5 is a flowchart of an example of an operational flow of a drowsiness prevention device according to a second exemplary embodiment.

FIG. 5 is a flowchart of an example of an operational flow of drowsiness prevention device 12 according to a second exemplary embodiment. For example, this processing is implemented by the CPU of drowsiness prevention device 12 reading out the program stored in the ROM and periodically performing the program, along with the activation of the engine of the vehicle. The operational flow illustrated in FIG. 5 is periodically and repeatedly performed. For the sake of simplicity, an example will be described where a psychological state of the occupant is an emotion. However, the following description is also applicable to a psychological state other than the emotion as the psychological state of the occupant.

The processing details in steps S1 to S10 and step S15 in FIG. 5 are the same as the processing details in the corresponding steps in FIG. 3. Hence, the descriptions thereof are omitted.

In step S11', drowsiness prevention device 12 obtains a changed amount of psychological state based on the first psychological state and the second psychological state (processing performed as controller 15).

In one example, the changed amount of psychological state is the magnitude of the change from the first psychological state to the second psychological state. For example, the changed amount of psychological state is a difference vector between an emotional vector indicating the first psychological state and an emotional vector indicating the second psychological state.

Figure 6:
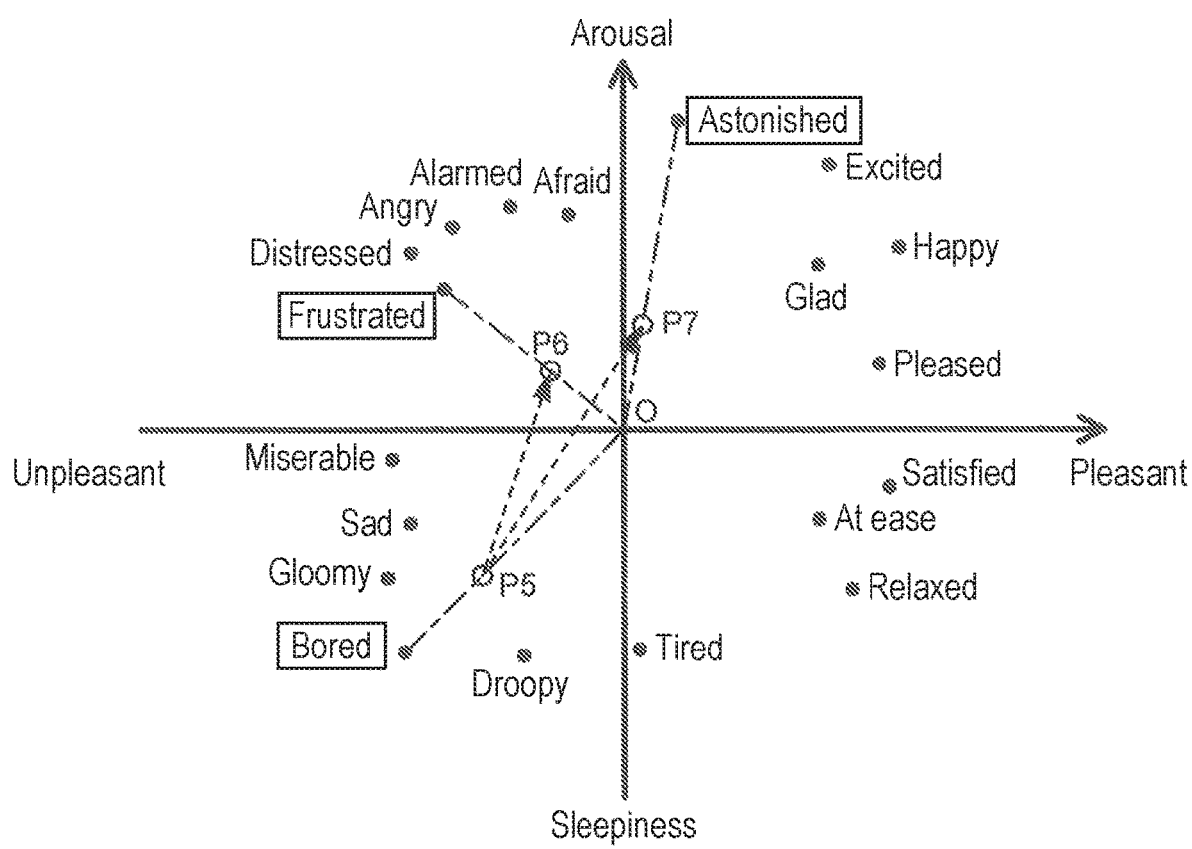
FIG. 6 illustrates emotional changes according to the second exemplary embodiment.

FIG. 6 illustrates emotional changes according to the second exemplary embodiment. In a similar manner to FIG. 4A and FIG. 4B, in FIG. 6, the horizontal axis and the vertical axis crossing at the origin O respectively represent a pleasantness axis and an arousal axis. Points (hereinafter, referred to as emotional points) corresponding to human emotions (such as "bored", "relaxed", "frustrated", and "astonished") are plotted.

For example, when the first psychological state and the second psychological state respectively represent the emotion indicated by emotional point P5 and the emotion indicated by emotional point P6, the changed amount of psychological state is difference vector P5P6 between emotional vector OP5 indicating the first psychological state and emotional vector OP6 indicating the second psychological state. In a similar manner, when the first psychological state and the second psychological state respectively represent the emotion indicated by emotional point P5 and the emotion indicated by emotional point P7, the changed amount of psychological state is difference vector P5P7 between emotional vector OP5 indicating the first psychological state and emotional vector OP7 indicating the second psychological state.

In another example, the changed amount of psychological state is the magnitude of the pleasantness axis component or arousal axis component of the difference vector.

Now, FIG. 5 is referred again. In step S13', drowsiness prevention device 12 determines the content and the level of the second warning, in accordance with the amount of psychological state change (processing performed as controller 15). For example, the level of the second warning is determined in accordance with the magnitude of the difference vector.

Emotional point P5 in FIG. 6 indicates the emotion of "bored" which is the same as emotional point P1 in FIG. 4A. The magnitude of emotional point P5 is less than that of emotional point P1. Emotional point P6 in FIG. 6 indicates the emotion of "frustrated" which is the same as emotional point P2 in FIG. 4A. The magnitude of emotional point P6 is less than that of emotional point P2.

In this case, the magnitude of difference vector P5P6 in FIG. 6 is less than the magnitude of difference vector P1P2 between emotional vectors OP1 and OP2 corresponding to emotional points P1 and P2, respectively, in FIG. 4A. In other words, the emotional change from emotional point P5 to emotional point P6 in FIG. 6 is less than the emotional change from emotional point P1 to emotional point P2 in FIG. 4A. In other words, the reaction of the occupant to the first warning is considered to be poor.

In this case, controller 15 determines the level of the second warning to be greater (higher intensity) than the case of the emotional change from emotional point P1 to emotional point P3. For example, when the second warning affects auditory sense, the level of sound is set to be proportional to the reciprocal of the magnitude of the difference vector. For example, when the magnitude of the difference vector is 0.3, the level of the sound is set to be 1/0.3=3.3 approximately, and when the magnitude of the difference vector is 0.9, the level of the sound is set to be 1/0.9=1.1 approximately. Accordingly, even to an occupant which has shown a poor emotional change, the second warning which is expected to be more effective to the occupant can be output to the occupant.

In a similar manner, emotional point P7 in FIG. 6 indicates the emotion of "astonished" which is the same as emotional point P3 in FIG. 4A. The magnitude of emotional point P7 is less than that of emotional point P3. In this case, in other words, the emotional change from emotional point P5 to emotional point P7 in FIG. 6 is less than the emotional change from emotional point P1 to emotional point P3 in FIG. 4A. Accordingly, also in this case, the level of the second warning is determined to be greater than the case of the emotional change from emotional point P1 to emotional point P3.

In one example, when the component of the difference vector along the pleasantness axis is a negative value, the second warning is not given.

Accordingly, when the emotion of the occupant is changed in the unpleasant direction in response to the first warning, a warning which makes the emotion of the occupant more unpleasant can be prevented.

In this way, drowsiness prevention device 12 according to the second exemplary embodiment determines the intensity of the second warning based on the magnitude of the change from the first psychological state to the second psychological state.

According to the second exemplary embodiment, in addition to the advantageous effects obtained in the first exemplary embodiment, it is possible to output, to an occupant, a warning with an intensity more suitable to the occupant.

Figure 7:
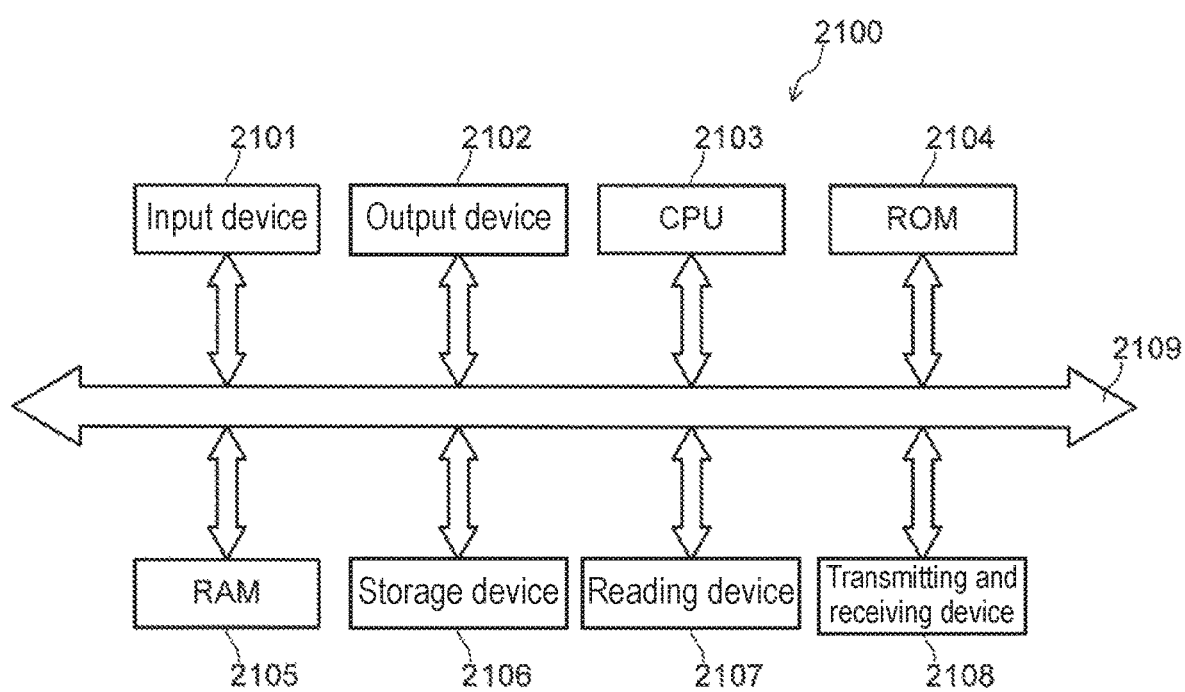
FIG. 7 illustrates an example of a hardware configuration of a computer.

FIG. 7 illustrates an example of a hardware configuration of a computer.

The functions of each function block in the exemplary embodiments and variations described above are implemented by a program executed by computer 2100.

As illustrated in FIG. 7, computer 2100 includes input device 2101 such as an input button and a touch pad, output device 2102 such as a display and a loudspeaker, central processing unit (CPU) 2103, read only memory (ROM) 2104, and random access memory (RAM) 2105. Moreover, computer 2100 includes storage device 2106 such as a hard disk device and a solid state drive (SSD), reading device 2107 which reads out information from a recording medium such as a digital versatile disk read only memory (DVD-ROM) and a universal serial bus (USB) memory, and transmitting and receiving device 2108 which performs communication over the network. Respective devices described above are interconnected via bus 2109.

Reading device 2107 reads out, from a recording medium which stores a program for realizing the functions of the respective function blocks, and allows storage device 2106 to store the program. Alternatively, transmitting and receiving device 2108 performs communication with a server device connected to the network, and stores, in storage device 2106, a program downloaded from the server device and realizing the functions of the respective function blocks.

Subsequently, CPU 2103 copies the program stored in storage device 2106 to RAM 2105, and sequentially reads out the commands included in the program from RAM 2105 for execution, thereby realizing the functions of the respective function blocks. Moreover, when executing the programs, information obtained in various processing described in each embodiment is stored in RAM 2105 or storage device 2106 and is used appropriately.

As another example, the function blocks such as psychological state estimator 14, controller 15, and drowsiness level estimator 16 of drowsiness prevention device 12 may also be realized as physical circuits such as dedicated integrated circuits (ICs) or large-scale integrations (LSIs).

Other Embodiments

In the second exemplary embodiment, controller 15 determines the content and the level of the second warning in accordance with the changed amount of psychological state. Such an embodiment is also possible in which the second exemplary embodiment is combined with the example in the first exemplary embodiment so that controller 15 determines the content and the level of the second warning based on both the first psychological state and the second psychological state or only the second psychological state.

In one example, the intensity or strength of the second warning is determined in accordance with the magnitude of the emotional vector which indicates the second psychological state. For example, when the second warning affects auditory sense, the level of sound is set to be proportional to the reciprocal of the magnitude of the emotional vector indicating the second psychological state. For example, when the magnitude of the emotional vector is 0.3, the level of the sound is set to be 1/0.3=3.3 approximately, and when the magnitude of the emotional vector is 0.9, the level of the sound is set to be 1/0.9=1.1 approximately. Accordingly, even to an occupant which has shown a poor emotion after the first warning, the second warning which is expected to be more effective on the occupant can be output to the occupant.

In one example, the content of the second warning is determined in accordance with the direction of the emotional vector which indicates the second psychological state. For example, when the type of the emotion indicated by the emotional vector is "astonished", controller 15 determines to generate cool air as the second warning.

In the first and second exemplary embodiments, the emotional vector is a two-dimensional vector. Alternatively, an embodiment is also possible in which an emotional vector of a given-dimension equal to or greater than three-dimensions is used.

The drowsiness prevention device according to the present disclosure is suitable to be applied to vehicles.

What is claimed is:

1. A drowsiness prevention device, comprising:
a processor; and
a memory coupled to the processor, the memory storing a program that, when executed by the processor, causes the drowsiness prevention device to:
estimate a psychological state of an occupant, based on a state of the occupant detected by a detection device;
cause an output device to output a first warning and a second warning which are for alerting the occupant;
estimate a first psychological state and a second psychological state of the occupant, the first psychological state being a psychological state of the occupant before the first warning is output, the second psychological state being a psychological state of the occupant after the first warning is output; and determine details of the second warning, based on both the first psychological state and the second psychological state, wherein an intensity of the second warning is determined based on a difference between a type of a first emotion corresponding to the first psychological state and a type of a second emotion corresponding to the second psychological state.

2. The drowsiness prevention device according to claim 1, wherein the second warning is determined in accordance with a change from the first psychological state to the second psychological state.

3. The drowsiness prevention device according to claim 2, wherein, upon determining that the change from the first psychological state to the second psychological state is not made, the second warning is determined to be different from the first warning.

4. The drowsiness prevention device according to claim 1, wherein, upon determining that the second psychological state is different from the first psychological state, the intensity of the second warning is determined based on a magnitude of a difference vector between a first vector indicating the first psychological state and a second vector indicating the second psychological state.

5. The drowsiness prevention device according to claim 1, wherein the program, when executed by the processor, further causes the drowsiness prevention device to:
estimate a level of drowsiness of the occupant; and
determine details of the first warning, based on a comparison between the level of drowsiness and a predetermined value.

6. The drowsiness prevention device according to claim 1, wherein each psychological state of the occupant is emotion.

7. The drowsiness prevention device according to claim 1, wherein the detection device is an image capturing device configured to capture an image of the occupant, and
wherein the program, when executed by the processor, further causes the drowsiness prevention device to:
estimate at least one psychological state of the occupant based on the image obtained from the image capturing device.

8. The drowsiness prevention device according to claim 1, wherein the output device includes at least one of a visual indicator, an audio indicator which outputs sound, an olfactory indicator which generates odor, and a tactile indicator which affects sense of touch.

9. A drowsiness prevention method performed by a drowsiness prevention device, the drowsiness prevention method comprising:
estimating a first psychological state of an occupant, based on a state of the occupant detected by a detection device;
causing an output device to output a first warning which is for alerting the occupant after the estimating of the first psychological state;
estimating a second psychological state of the occupant, based on the state of the occupant detected by the detection device, the second psychological state being a psychological state of the occupant after the first warning is output;
determining details of a second warning which is for alerting the occupant, based on both the first psychological state and the second psychological state; and
causing the output device to output the second warning after the determining of the details of the second warning,
wherein an intensity of the second warning is determined based on a difference between a type of a first emotion corresponding to the first psychological state and a type of a second emotion corresponding to the second psychological state.

10. A non-transitory recording medium on which a program is stored, the program being executed by a computer included in a drowsiness prevention device, the program causing the computer to execute:
estimating a first psychological state of an occupant, based on a state of the occupant detected by a detection device;
causing an output device to output a first warning which is for alerting the occupant after the estimating of the first psychological state;
estimating a second psychological state of the occupant, based on the state of the occupant detected by the detection device, the second psychological state being a psychological state of the occupant after the first warning is output;
determining details of a second warning which is for alerting the occupant, based on both the first psychological state and the second psychological state; and
causing the output device to output the second warning after the determining of the details of the second warning,
wherein an intensity of the second warning is determined based on a difference between a type of a first emotion corresponding to the first psychological state and a type of a second emotion corresponding to the second psychological state.

* * * * *